(12) United States Patent
Miller

(10) Patent No.: US 7,621,908 B2
(45) Date of Patent: Nov. 24, 2009

(54) CATHETER FOR MANIPULATION OF THE ESOPHAGUS

(76) Inventor: Steven W. Miller, 2501 SW. 11th Ct., Boynton Beach, FL (US) 33426

( * ) Notice: Subject to any disclaimer, the term of this patent is extended or adjusted under 35 U.S.C. 154(b) by 432 days.

(21) Appl. No.: 11/283,104

(22) Filed: Nov. 18, 2005

(65) Prior Publication Data

US 2007/0118105 A1     May 24, 2007

(51) Int. Cl.
    *A61B 18/18*     (2006.01)
    *A61M 29/00*     (2006.01)
(52) U.S. Cl. ............... 606/32; 606/41; 606/191
(58) Field of Classification Search .......... 606/41, 606/34, 32, 191; 600/146–151; 128/898
See application file for complete search history.

(56) References Cited

U.S. PATENT DOCUMENTS

| | | | |
|---|---|---|---|
| 4,581,017 A | 4/1986 | Sahota | |
| 4,930,521 A * | 6/1990 | Metzger et al. | 607/145 |
| 5,087,244 A | 2/1992 | Wolinsky et al. | |
| 5,170,803 A | 12/1992 | Hewson et al. | |
| 5,531,776 A * | 7/1996 | Ward et al. | 607/105 |
| 5,570,671 A * | 11/1996 | Hickey | 600/486 |
| 5,588,961 A | 12/1996 | Leone et al. | |
| 5,681,344 A | 10/1997 | Kelly | |
| 5,971,983 A * | 10/1999 | Lesh | 606/41 |
| 6,095,990 A | 8/2000 | Parodi | |
| 6,148,222 A | 11/2000 | Ramsey, III | |
| 6,221,049 B1 | 4/2001 | Selmon et al. | |
| 6,259,938 B1 * | 7/2001 | Zarychta et al. | 600/380 |
| 6,497,704 B2 | 12/2002 | Ein-Gal | |
| 6,582,388 B1 | 6/2003 | Coleman et al. | |
| 6,754,536 B2 * | 6/2004 | Swoyer et al. | 607/40 |
| 6,913,604 B2 | 7/2005 | Mihalik et al. | |
| 7,041,095 B2 | 5/2006 | Wang et al. | |
| 7,047,074 B2 | 5/2006 | Connelly et al. | |
| 7,052,493 B2 | 5/2006 | Vaska et al. | |
| 7,089,063 B2 | 8/2006 | Lesh et al. | |
| 2002/0165461 A1 * | 11/2002 | Hayzelden et al. | 600/523 |

\* cited by examiner

*Primary Examiner*—Lee S Cohen
(74) *Attorney, Agent, or Firm*—McHale & Slavin, P.A.

(57) ABSTRACT

An esophageal catheter for displacing and fixing the position of the esophagus in relation to the atrium of the heart is composed of a long flexible tube to be inserted into the esophagus. A control wire is associated with the tube to change the shape of the catheter and displace the esophagus relative to the heart to reduce the risk of an esophageal fistula resulting from atrial RF ablation.

8 Claims, 5 Drawing Sheets

CATHETER FOR MANIPULATION OF THE ESOPHAGUS

FIELD OF THE INVENTION

This invention relates to heart surgery and more particularly to RF (radio frequency) catheter ablation of atrial fibrillation (AF) and other atrial arrythmias.

BACKGROUND OF THE INVENTION

The goal of the surgical treatment of atrial fibrillation is to block or interfere with impulses radiating from ectopic foci inside the pulmonary veins that triggered atrial fibrillation. Among the first intra-heart surgical treatments for atrial fibrillation was demonstrated by the Leipzig group in a procedure referred to as, endocardial linear lesion, to connect the pulmonary vein to the mitral annulus during open heart surgery.

The Mayo Clinic is known for another open heart surgical procedure, termed the Maze procedure, in which multiple cuts are created in the atrial muscle in a maze pattern. These cuts produce scar tissue which does not carry electrical impulses and as a result the stray impulses causing atrial fibrillation are eliminated producing a normal coordinated heartbeat.

More recently, cardiology specialists called, electrophysiologists, have used cardiac catheters to ablate the heart tissue without the need for open heart surgery. In this procedure, an RF catheter is inserted into the atrium and a series of ablations or burns are performed around the mouth of the pulmonary vein and the left atrial wall. The ablations also form scar tissue blocking stray electrical impulses to restore normal heartbeat. During RF catheter ablation, lesion depth, extension and volume are related to the design of the ablation electrode and the RF power delivered.

Among the complications that may arise is pulmonary vein stenosis, if the ablations are too close to the mouth of the pulmonary vein. Another serious and, possibly fatal, complication is atrial-esophageal fistula caused by thermal penetration of the walls of the atrium and esophagus. The atrial-esophageal fistula can lead to pericarditis, or fluid between the outer wall of the heart and the pericardium restricting the heartbeat, hemorrhage, or other life threatening conditions.

The atrial-esophageal fistula or hole in the esophageal wall may result, in part, from simple anatomy and the RF power needed to develop ablations, as well as the design of the catheter electrode tip and other contributing factors, such as movement of the esophagus during the procedure.

The esophagus is located at the center of the posterior mediastinum and is separated from the atrium only by the pericardial sac and/or a thin layer of fatty tissue and may be in contact with the atrium. The left atrium wall thickness is about 2-4 mm and the esophagus thickness is about 2-3 mm. The esophagus is supported at it's upper end near the trachea and transits the diaphragm to connect with the stomach. The esophagus is supported at its lower end by the diaphragm. The thoracic portion of the esophagus between the trachea and the stomach is mobile and loosely restrained only by soft tissue. This allows the esophagus to move in response to swallowing food, cardiac and lung movement, as well as upper body movements. This flexibility of the esophagus complicates the problem of avoiding atrial-esophageal fistula.

DESCRIPTION OF THE PRIOR ART

Currently, several techniques are employed by the electrophysiologists to reduce the likelihood of an atrial-esophageal fistula developing during the RF atrial ablation. The most comprehensive technique involves a pre-operative procedure of developing a 3-D map of the operative field by CT scan or MRI displayed with real time 3-D electroanatomical maps to reveal the cardiac anatomical relationships. This mapping system may or, may not, be used with a contrast medium in the esophagus to better locate the position of the esophagus. The mapping systems allow the ablations to be precisely plotted on the atrium wall. The locations of some ablations may be changed or adjusted because of anatomical considerations. Contrast placement in the esophagus may be used independently of CT/MRI to allow real time visualization of the esophagus.

In some cases, the area of the atrium traversed by the esophagus is avoided during the ablation procedure when the outcome is not comprised.

The electrical energy of the electrode can be controlled, eg., reducing power in the vicinity of the esophagus. However, the adjustment is not significant.

Therefore, what is needed in the art is a device for controlling the location of the esophagus in relation to the atrium during RF catheter ablation.

SUMMARY OF THE INVENTION

Accordingly, it is a primary objective of the instant invention to provide an esophageal catheter capable of moving and restraining the esophagus away from certain areas overlying the posterior portion of the heart.

It is a further objective of the instant invention to provide a naso-gastric catheter capable of laterally displacing an intermediate portion of the esophagus along the longitudinal axis.

It is yet another objective of the instant invention to provide a control wire for insertion through an esophageal catheter to control the longitudinal shape.

It is a still further objective of the invention to provide an esophageal catheter with embedded control wires for changing longitudinal direction.

It is yet another objective of the invention to utilize the support provided to the esophagus in the area of the trachea and the area of the diaphragm to anchor the ends of the esophagus and induce lateral movement of the esophagus in the mid-portion dorsal to the atrium.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
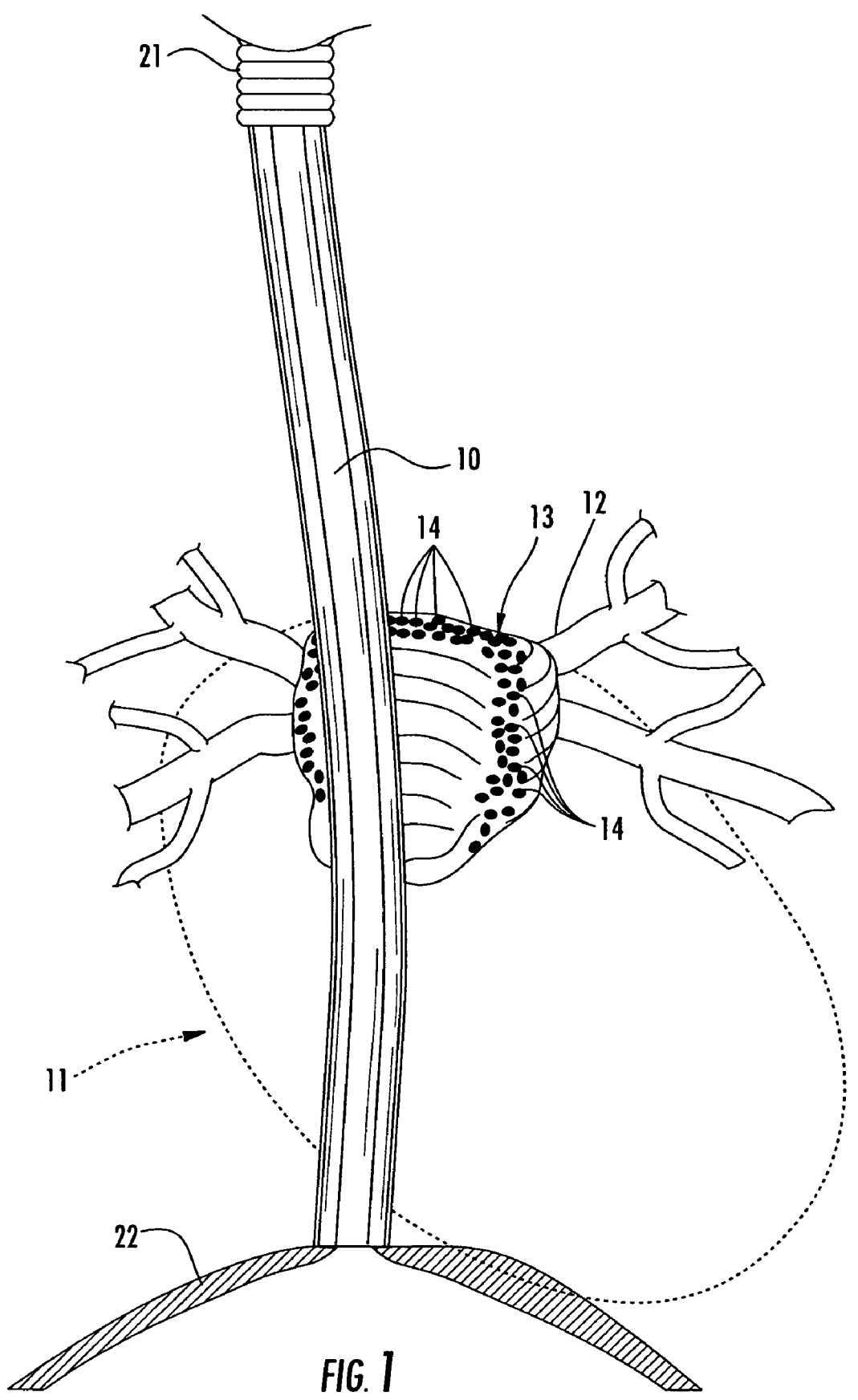
FIG. 1 is a representation of the heart and esophagus showing a pattern of optimal ablation lesions.

In FIG. 1, a posterior view of the patient shown with the heart 11 in phantom lines lying in front of the esophagus 10. The esophagus is supported by the trachea 21 at one end and by the diaphragm 22 at the other end. Normal anatomical variation in the exact location of the atrium-esophageal relationship does occur. The right pulmonary vein 12 enters the atrium 13 and the desired pattern of optimal ablation lesions 14 are shown as they might appear in the mapping procedure. When viewing these proposed ablation lesions 14, either pre-operatively or intra-operatively, the surgeon may decide to change the location of some of the ablations because of the proximity to the esophagus 10. If a particular ablation(s) is considered necessary regardless of the location of the esophagus, the RF power to the electrode may be reduced.

Figure 2:
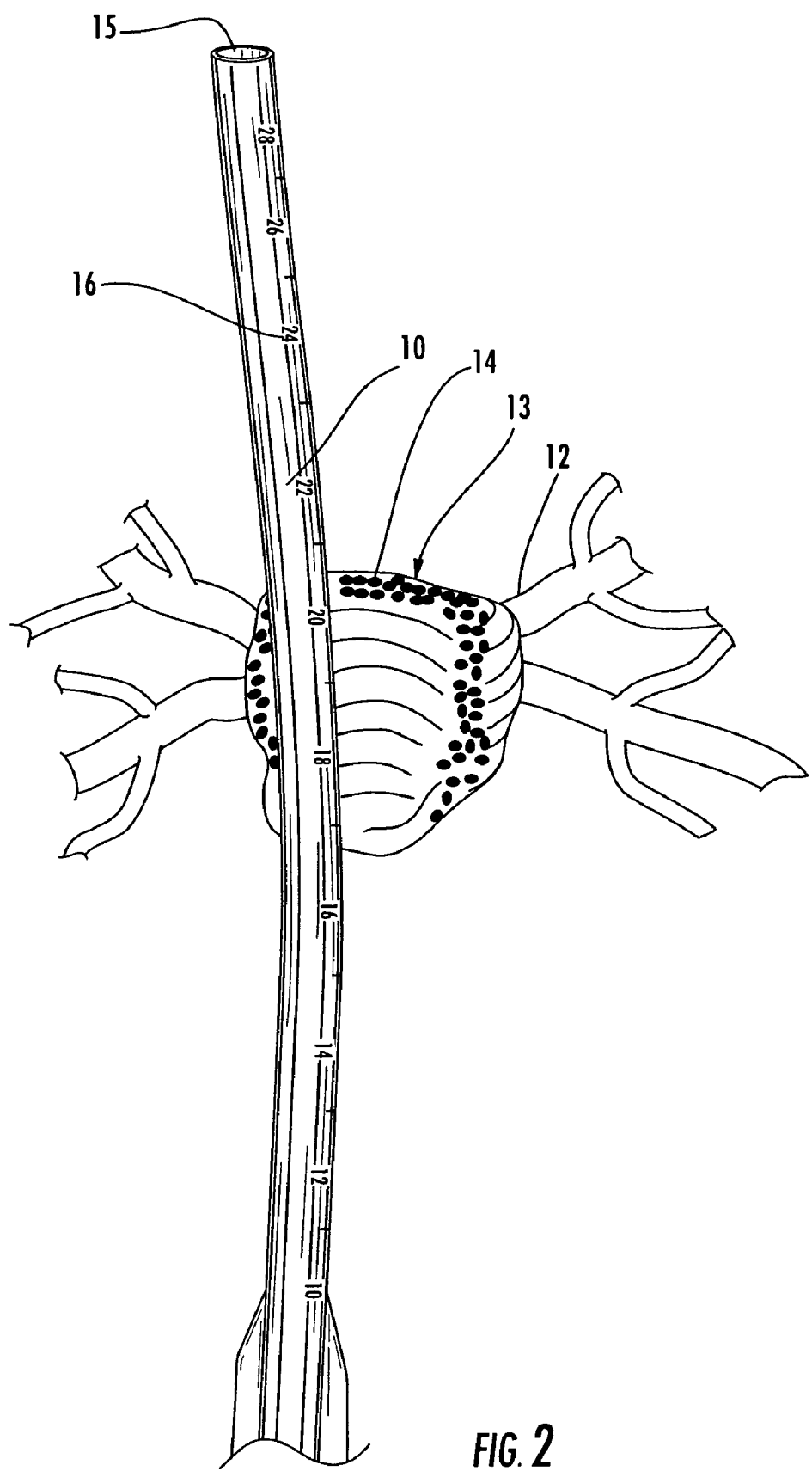
FIG. 2 is a representation of the heart and esophagus of FIG. 1 with an esophageal catheter inserted.

To manage the surgical field to eliminate the possibility of an esophageal fistula, an esophageal catheter or tube 15 is inserted through the mouth or nose into the esophagus 10 and through the length of the esophagus past the diaphragm 22, as shown in FIG. 2. The catheter 15 may include a radiologic marker or markers 16 to improve visualization of the location of the catheter 15 and esophagus 10.

Figure 3:
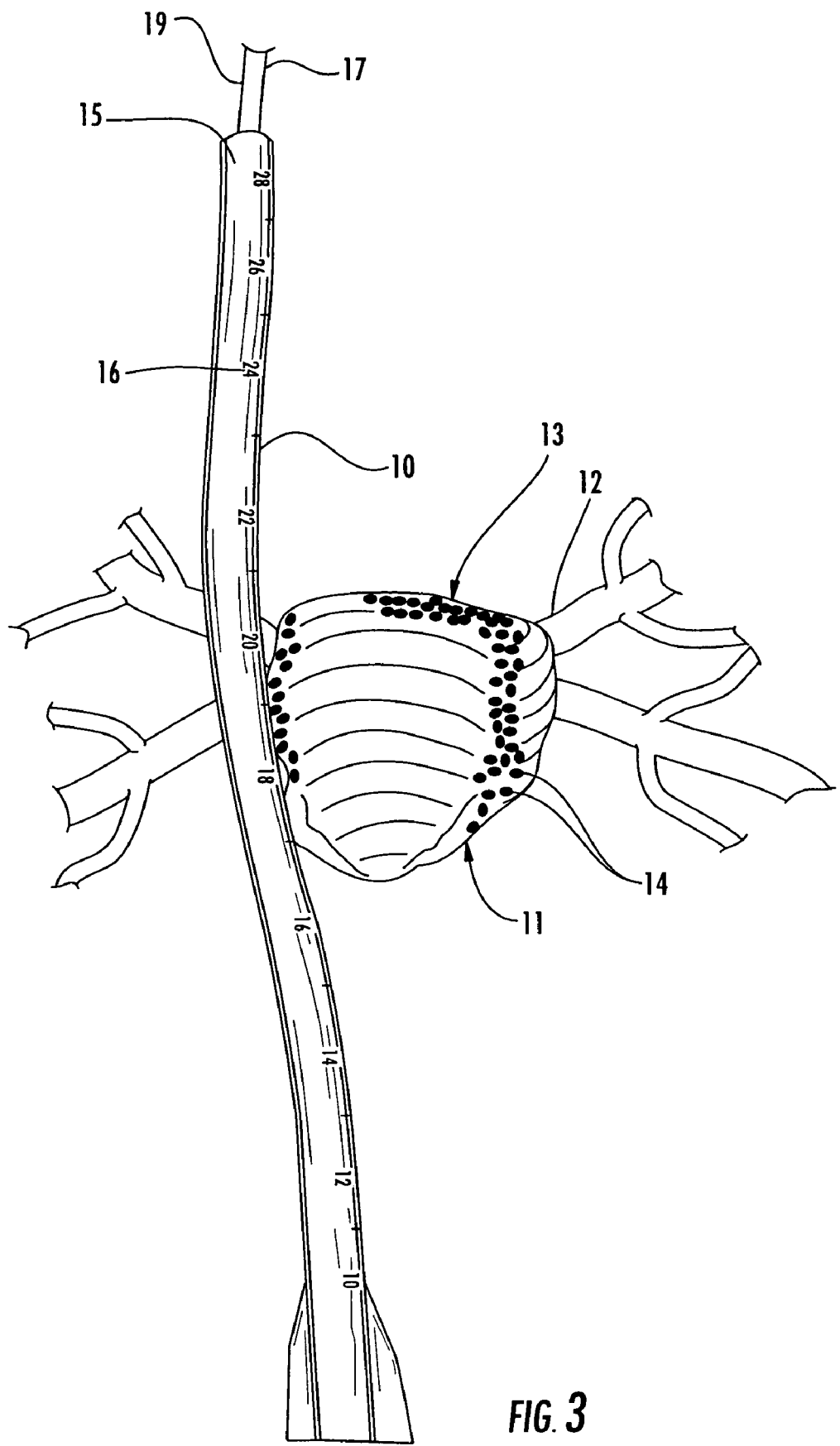
FIG. 3 is a representation of the heart and esophagus of FIG. 1 with the control wires changing the direction of the catheter and esophagus.
Figure 4:
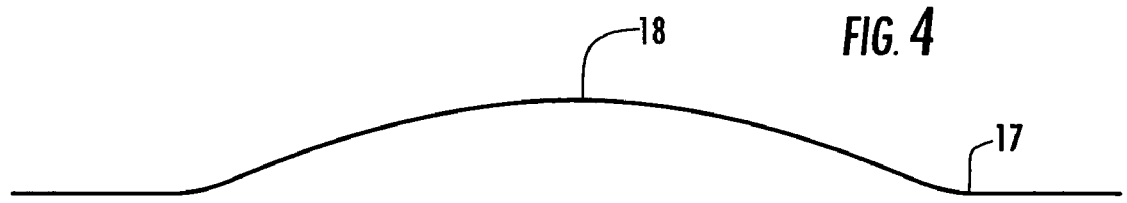
FIG. 4 is a representation of one of the control wires of FIG. 3.
Figure 5:
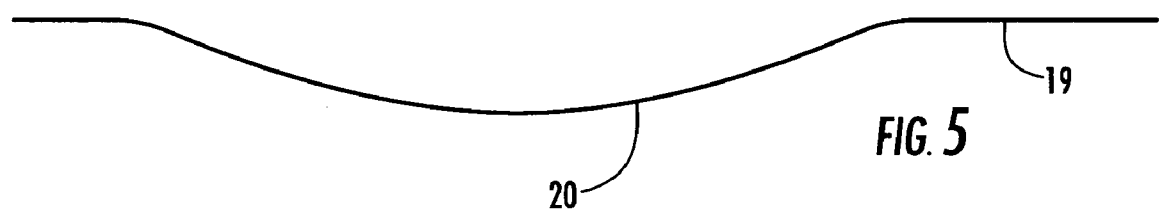
FIG. 5 is a representation of another of the control wires of FIG. 3.

To move the esophagus laterally, in the surgical field, and to fix the displaced portion of the esophagus beyond the area of thermal lesions, a control wire 17 is inserted through the lumen of the catheter 15. As shown in FIGS. 4 and 5, the control wires have a preformed curved intermediate portion 18. As the curved portion moves through the catheter, the catheter is displaced along it's longitudinal axis to follow the curve of the control wire. The control wire may be round, flattened, single strand or multi-strand, such as a guide wire. The control wire 17 is manipulated within the catheter to place the curved portion 18 near the atrium and to rotate the control wire to displace the catheter and esophagus away from the ablation lesions 14 laterally and posteriorly as the patient's anatomy permits, as shown in FIG. 3. Depending on the relative size of the catheter lumen 21 and the control wire, a second control wire 19 may be used having a similar curved portion 20. The control wires 17 and 19 may be used in conjunction with each other to produce one curve or, independently, to form the catheter in other shapes. The use of separate control wires allows the catheter to remain in place, once inserted, and to be bent in the area dictated by the anatomy of each individual patient. As shown in FIG. 3, the curvature of the catheter is left lateral however, the control wires may be manipulated to force the esophagus in the dorsal direction away from the heart or to the right laterally.

Figure 6:
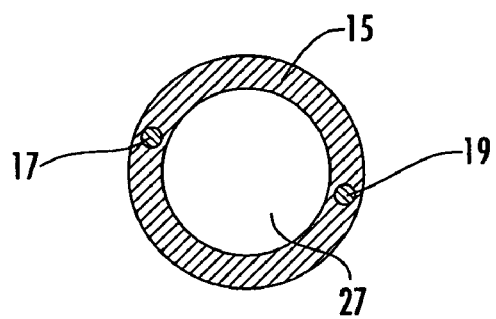
FIG. 6 is a cross section of another esophageal catheter with control wires in the sidewall.
Figure 7:
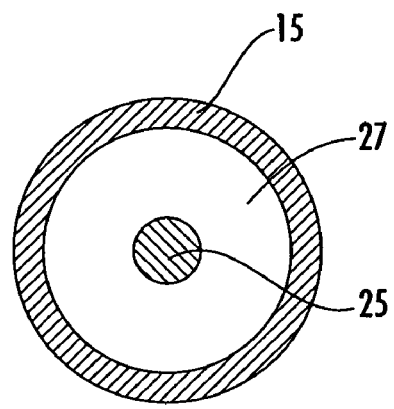
FIG. 7 is a cross section of the esophageal catheter with the control wire in the lumen.
Figure 8:
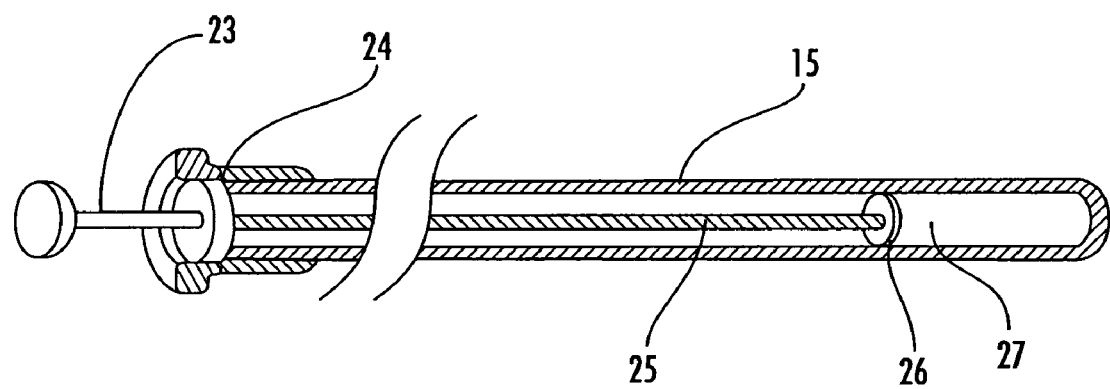
FIG. 8 is a partial longitudinal cross section of another embodiment of the esophageal catheter and control wire.

As shown in FIG. 6, FIG. 7 and FIG. 8, the catheter 15 has control wires attached to the sidewall at discrete points 26 along the catheter. By differential movement of the control wires and the catheter, respectively, as shown in FIG. 8, the longitudinal shape of the catheter can be changed. In FIG. 8, either the plunger 23 or the barrel 24 is moved relative to the other, thereby shortening one member in relation to the other and causing the catheter to bend in the mid-portion. In FIG. 6, separate control wires 17 and 19 located in the sidewall of the catheter 15 can be moved to bend the catheter in different directions. In FIG. 7 the control wire 25 is located in the lumen 27 and attached to the side wall at 26. The catheter may be rotated in the esophagus to move the esophagus, as desired.

Also, control wires made from shape retaining memory materials, such as Nitinol, can be used. These wires are preformed at a certain temperature with the desired curve and then cooled and straightened. When the catheter is placed in the body, the wires assume their original curved shape as they become heated.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An esophageal catheter for use in cardiac catheter ablation comprising an elongated flexible tube constructed and arranged to be inserted in an esophagus and extend to overlie the heart, said tube including a first control wire extending longitudinally through a lumen of said tube, said first control wire having a curved portion, said curved portion of said first control wire constructed and arranged to displace said tube laterally in the area of the heart thereby displacing at least a portion of said esophagus relative to the heart, a second control wire extending longitudinally through said lumen of said tube, said second control wire having a second curved portion, said second curved portion constructed and arranged to displace said tube laterally in the area of the heart, thereby displacing at least a portion of said esophagus relative to the heart.

2. The esophageal catheter for use in cardiac catheter ablation of claim 1 wherein said first and said second control wires are freely slidable through said lumen in said tube to position said first and said second curved portions with respect to said heart.

3. The esophageal catheter for use in cardiac catheter ablation of claim 1 wherein said first control wire being rotatably disposed in said lumen.

4. The esophageal catheter for use in cardiac catheter ablation of claim 1 wherein said tube has a longitudinal sidewall, a distal end of said first control wire being attached to said sidewall.

5. The esophageal catheter for use in cardiac catheter ablation of claim 1 wherein said tube has a longitudinal sidewall, a distal end of said first control wire being attached to said sidewall and a distal end of said second control wire attached to said sidewall.

6. The esophageal catheter for use in cardiac catheter ablation of claim 1 wherein said flexible tube includes at least one radiologic marker.

7. An esophageal catheter for use in surgical treatment of atrial fibrillation by cardiac catheter ablation comprising an elongated flexible tube constructed and arranged to be inserted into the esophagus and extend to at least the diaphragm, an elongated lumen in said tube, a pair of control wires adapted to be slidably disposed in said lumen, said pair of control wires having a distal end and a proximal end, said pair of control wires each having a curved portion intermediate said distal end and said proximal end, each said curved portion adapted to overlie the heart whereby manipulation of said control wires displace said esophagus with respect to the heart.

8. A method of using an esophageal catheter in a surgical procedure for treatment of atrial fibrillation by atrial ablation comprising the steps of:
 a) providing a flexible esophageal catheter;
 b) inserting said esophageal catheter into the esophagus a distance to overlie the heart;
 c) providing at least one control wire with a curved portion intermediate the ends;
 d) inserting said control wire into a lumen within said catheter at least a distance to dispose said curved portion near the atrium of said heart;
 e) manipulating said control wire whereby said curved portion moves said catheter and said esophagus away from said heart;
 f) performing an ablation procedure on said heart.

* * * * *